United States Patent [19]
Lushbaugh et al.

[11] Patent Number: 4,758,521
[45] Date of Patent: Jul. 19, 1988

[54] ASSAY OF KETONES IN AMBIENT AIR

[75] Inventors: Robley E. Lushbaugh; Richard A. Conway, both of Charleston; Joe E. Neff, South Charleston, all of W. Va.

[73] Assignee: Union Carbide Corporation, Danbury, Conn.

[21] Appl. No.: 702,318

[22] Filed: Feb. 15, 1985

[51] Int. Cl.⁴ .................. G01N 21/75; G01N 31/22
[52] U.S. Cl. ................... 436/128; 436/130; 436/167; 422/60; 422/88; 73/863.21
[58] Field of Search ............ 422/59, 60, 83, 88; 436/128, 130, 167; 73/23, 53, 61 R, 863.21; 55/74

[56] References Cited

U.S. PATENT DOCUMENTS

| | | | |
|---|---|---|---|
| Re. 29,101 | 1/1977 | Amagi et al. | 423/449 |
| 2,653,959 | 9/1953 | Moore et al. | 55/61 |
| 3,089,250 | 5/1963 | Victor | 55/74 X |
| 3,778,387 | 12/1973 | Urbanic et al. | 55/74 X |
| 3,870,492 | 3/1975 | Guild | 55/387 |
| 3,917,806 | 11/1975 | Amagi et al. | 423/449 |
| 4,003,257 | 1/1977 | Fletcher et al. | 436/178 X |
| 4,021,211 | 5/1977 | Turek et al. | 55/74 X |
| 4,047,906 | 9/1977 | Murakami et al. | 55/79 |
| 4,058,457 | 11/1977 | Manes | 502/22 X |
| 4,061,477 | 12/1977 | Murakami et al. | 55/79 |
| 4,139,489 | 2/1979 | Mizuno et al. | 252/411 R |
| 4,149,023 | 4/1979 | Mizuno et al. | 13/7 |
| 4,207,082 | 6/1980 | Okamoto et al. | 55/60 |
| 4,259,094 | 3/1981 | Nagai et al. | 55/181 |
| 4,277,259 | 7/1981 | Rounbehler et al. | 55/270 |
| 4,289,505 | 9/1981 | Hardison et al. | 55/180 X |
| 4,350,037 | 9/1982 | Higham | 73/23 |
| 4,389,372 | 6/1983 | Lalin | 422/88 |

Primary Examiner—Barry S. Richman
Assistant Examiner—Lynn M. Kummert
Attorney, Agent, or Firm—Robert J. Feltovic

[57] ABSTRACT

A method of assaying ketones in ambient air comprising contacting the air with beaded activated carbon followed by desorption with a solvent and analysis of the solvent solution for ketone content has been developed which provided superior results over prior art adsorbents, particularly when the sampling operation is conducted in the presence of humid air.

7 Claims, 1 Drawing Sheet

U.S. Patent
Jul. 19, 1988
4,758,521
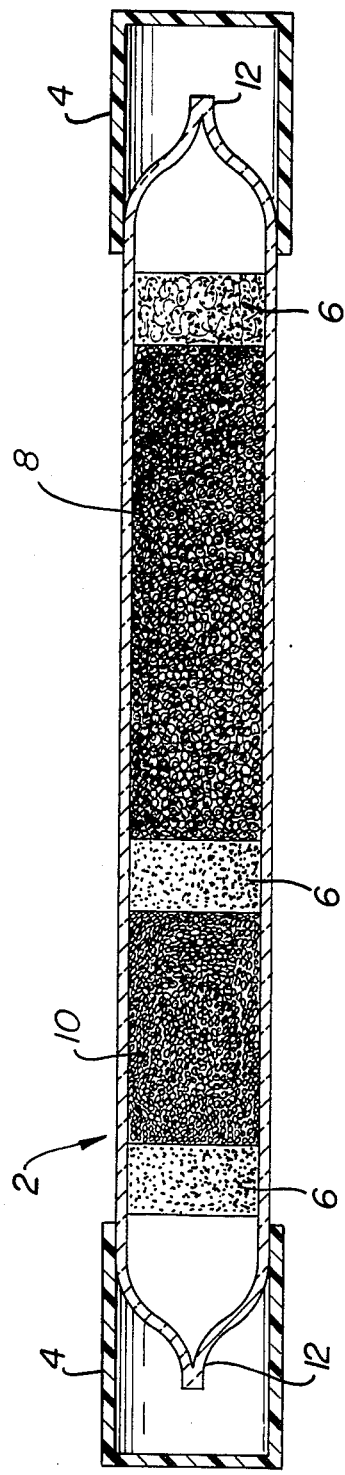

ASSAY OF KETONES IN AMBIENT AIR

BACKGROUND OF THE INVENTION

This invention pertains to the assay of ketones in ambient air and more particularly to the use of bead activated carbon in said assay.

BACKGROUND ART

It has been stated by the National Institute of Occupational Safety and Health that toxicologic information for most ketones is deficient. The possibility therefore exists that occupational exposure to ketones could produce carcinogenic, mutagenic or teratogenic effects. It follows that valid and reproducible techniques for measuring airborne ketones are needed.

In the past air sampling tubes filled with coconut shell charcoal have been used to collect airborne samples of ketones. However, it has been found that many ketones are not stable on coconut shell charcoal. Recovery of methyl ethyl ketone and cyclohexanone from coconut shell carbon for example was found to be poor thus rendering analytical methods with this substance undesirable. Other reports also indicated that several other ketones were unstable on coconut shell carbon unless samples were stored in a freezer.

It is therefore an object of this invention to provide a method for assaying ketones in ambient air.

Other objects will become apparent to those skilled in the art upon a further reading of the specification.

SUMMARY OF THE INVENTION

A method of assaying ketones in ambient air has been found which comprises:

(A) Contacting a known volume of ambient air containing ketones at ambient temperature with an excess of beaded activated carbon whereby said ketones are absorbed onto the bead activated carbon;

(B) Contacting the beaded activated carbon containing absorbed ketones from step (A) with a solvent for ketones whereby said absorbed ketones are desorbed from the bead activated carbon forming a solution of said ketones in said solvent;

(C) Recovering the solution of ketones from step (B) and analyzing same for ketone content.

The ketones which lend themselves to assay by this invention can be delineated by the generic formula:

wherein each of X and Y can be monovalent aliphatic cycloaliphatic or aromatic radicals having up to about 7 carbon atoms.

Exemplary aliphatic ketones include:
  acetone
  methyl ethyl ketone
  diethyl ketone
  methyl isobutyl ketone
  ethyl butyl ketone
  diisobutyl ketone
  methyl phenyl ketone,
  and the like Suitable cycloaliphatic ketones include cyclopentanone, cyclohexanone, cycloheptanone and the like.

Representative aromatic ketones include acetophenone, propiophenone, benzophenone, and the like.

In addition substituted ketones and diketones can be assayed, such as, mesityl oxide, diacetyl, acetyl acetone, phorone, isophorane, and the like.

The term "beaded activated carbon" is used herein to mean spherical beads of activated carbon prepared from porous pitch by a process developed by Kureha Chemical of Japan and commercially available from Union Carbide Corporation as PURASIV ®HR. The process is described in U.S. Pat. No. 3,917,806 which is incorporated herein by reference.

Preferred desorption solvents include: carbon disulfide and carbon disulfide with 1.0% by volume methanol.

DESCRIPTION OF THE INVENTION

Although this invention is not limited to any specific apparatus or containers, it has been found convenient to collect samples of air for assay in sample tubes comprising an open-ended tube filled in sequence with a porous plug, a first section of beaded activated carbon, a second porous plug, a second section filled with beaded activated carbon whose volume is at least one-half the volume of the first section, followed by a third porous plug.

The porous plugs can be fabricated from any inert porous material such as polyurethane foam, glass wool, polystyrene foam, stainless steel screen, and the like.

The material of construction of the open ended tube is not narrowly critical but for convenience can be glass, stainless steel, and the like.

To prevent premature absorption by the sample tube both ends can be capped with a suitable closure means which can be readily removed for sampling and replaced after exposure of the tube and tube contents to ambient air containing ketones.

The FIGURE is a sampling tube, 2, having closures, 4, a first, second and third porous plug, 6, a first beaded activated carbon section, 8, and a second beaded activated carbon section, 10. The flame sealed ends, 12, are broken prior to sampling.

The invention is further described in the Examples which follow. All parts and percentages are by weight unless otherwise described.

EXAMPLE 1

Preparation of Sample Tube

A piece of glass tubing (6 mm O.D.) 60 mm in length was fire polished at both ends. A piece of high purity glass wool was inserted in one end. One hundred mg. of beaded activated carbon (PURASIV ®HR) was packed into the tube from the other end. This amount of beaded activated carbon occupied about 15 mm of the glass tube and constitutes the first section of adsorbent. This is the primary adsorption section. Another piece of glass wool was packed in the glass tube retaining the beaded activated carbon in place. Next 50 mg. of beaded activated carbon was packed into the glass tube length. This is the backup adsorption section. Finally the last piece of glass wool was inserted into the tube holding the second section of absorbent in place. Both ends of the glass tube were sealed by placing 7/32 inch Caplugs ® on them.

Caplugs are sold by the Protective Closures Co., Inc. Buffalo N.Y.

EXAMPLE 2

Collecting Air Samples

In order to take an air sample for ketone assay using the sample tube fabricated as in Example 1, the Caplugs are first removed from the ends of the sample tube and the sealed ends opened. The end of the sample tube closest to the backup adsorption section is then connected to a portable personal sampling pump by means of a 3 foot length of surgical rubber tubing. The sampling pump is now activated pulling a known volume of ambient air through the sample tube at a known rate and at ambient temperature. The volume of air is previously determined during laboratory validation of the ketone to be assayed. When this predetermined volume of air has passed through the sampling tube, the tube is recapped at both ends, marked for identification and stored for analysis. The time duration between sampling and analysis and the storage conditions can be determined during prior laboratory validation studies.

EXAMPLE 3

Analysis of Sampled Ketones

The Caplugs on the end of the sampling tube nearest the primary adsorption section is removed followed by the removal of the glass wool plug. The beaded activated carbon from the primary adsorption section is then transferred into a glass vial for desorption of any adsorbed ketone. The second glass wool plug is next removed and the beaded activated carbon from the backup adsorption section transferred to a second desorption vial.

A known volume of desorption solvent is next pipetted into each of the desorption vials which are promptly capped to prevent loss of solvent. The nature of the solvent and the respective volumes for each vial are previously determined during prior laboratory validation studies.

The desorption vials are shaken by hand or mechanical shaker to insure that all of the beaded activated carbon comes into contact with the desorption solvent.

The desorption vials are allowed to stand for a specified time, with ocassional shaking or mechanical shaking to allow the beaded activated carbon to desorb. This time period is also determined beforehand during the prior laboratory validation study.

The solvent extracts, from the desorption vials containing extracts of the primary and backup sections respectively, are now analyzed by gas chromatographic analysis for ketone analytic content. If the amount of analyte from the backup section exceeds 25 percent by weight of the amount of ketone analyte from the primary section, overloading of the sampling tube is indicated and that sample is discarded. If this FIGURE is less than 25 percent, the amount of ketone analyte in the primary and backup are added. The total sample weight and the total air sample volume are then used to calculate the average air concentration in parts per million for the sample.

The procedure outlined supra provides general guidelines for the ketone assay. Many variables have to be considered for each specific industrial hygiene sampling problem. These variables may include:

(1) The properties of the analyte, such as, molecular weight, reactivity, boiling point, density, and the like;

(2) The expected concentration of analyte in the air sampled;

(3) The amount of beaded activated carbon used in each sampling tube;

(4) The sampling time and volume of air needed to collect a sufficient quantity of analyte for analysis, (5) The humidity level of the air being sampled since very high humidity reduces the adsorption capacity of the beaded activated carbon;

(6) The presence of other compounds in the air being sampled since higher molecular weight compounds tend to displace lower molecular compounds from the beaded activated carbon, and (7) The stability of the ketone after adsorption on the beaded activated carbon.

Control A. Recovery of Cyclohexanone from Coconut Shell Charcoal

Using the sampling tubes described previously with the exception that Coconut Shell Carbon was used in place of beaded activated carbon, three tubes were evaluated by injecting 1890 micrograms of cyclohexanone into the front of each tube after which 6 liters of humidified air was pulled through the tube. Each sampling tube was capped and stored at room temperature overnight. After storage, the front and backup sections of each tube were transferred into separate desorption vials, 2 ml of carbon disulfide was added to each vial and the amount of analyte was determined using the analytical procedure described in Example 3, analysis of Sampled Ketones. The data from the recovery of cyclohexanone are presented in Table 1.

TABLE 1

(Control A)
RECOVERY OF CYCLOHEXANONE
FROM COCONUT SHELL CHARCOAL

| Sample No. | Cyclohexanone Loaded Micrograms | Cyclohexanone Recovered Micrograms | Recovered % |
| --- | --- | --- | --- |
| 1 | 1890 | 976 | 51.6 |
| 2 | 1890 | 1102 | 58.3 |
| 3 | 1890 | 1088 | 57.6 |

EXAMPLE 4

Recovery of Cyclohexanone from Beaded Activated Carbon

Using the sampling tubes described previously where beaded activated carbon was charged as the adsorbent, three sampling tubes were evaluated by injecting 1890 micrograms of cyclohexanone into the front of each tube after which 6 liters of humidified air were pulled through each tube. These tubes were capped and stored overnight at room temperature and analyzed using the same procedure described in Control A, Recovery of Cyclohexanone from Coconut Shell Charcoal. Table 2 shows this data.

TABLE 2

(Example 4)
RECOVERY OF CYCLOHEXANONE
FROM BEADED ACTIVATED CARBON

| Sample No. | Cyclohexanone Loaded Micrograms | Cyclohexanone Recovered Micrograms | Recovered % |
| --- | --- | --- | --- |
| 1 | 1890 | 1504 | 79.6 |
| 2 | 1890 | 1540 | 81.5 |

TABLE 2-continued
(Example 4)
RECOVERY OF CYCLOHEXANONE
FROM BEADED ACTIVATED CARBON

| Sample No. | Cyclohexanone Loaded Micrograms | Cyclohexanone Recovered Micrograms | Recovered % |
|---|---|---|---|
| 3 | 1890 | 1566 | 82.9 |

Control B Recovery of Methyl Ethyl Ketone From Coconut Shell Charcoal

The procedure described in Control A was used with the exception that 2406 micrograms of methyl ethyl ketone was injected onto the coconut shell charcoal sample tube. The data are presented in Table 3.

TABLE 3
(Control B)
RECOVERY OF METHYL ETHYL KETONE
FROM COCONUT SHELL CHARCOAL

| Sample No. | Methyl Ethyl Ketone Loaded Micrograms | Methyl Ethyl Ketone Recovered Micrograms | Recovered % |
|---|---|---|---|
| 1 | 2406 | 1306 | 54.2 |
| 2 | 2406 | 1106 | 46.0 |
| 3 | 2406 | 1208 | 50.2 |

EXAMPLE 5

Recovery of Methyl Ethyl Ketone from Beaded Activated Carbon

The procedure described in Control A was used with the exception that 2406 micrograms of Methyl ethyl ketone was injected onto the beaded activated carbon sample tube. The data is presented in Table 4.

TABLE 4
(Example 5)
RECOVERY OF METHYL ETHYL KETONE
FROM BEADED ACTIVATED CARBON

| Sample No. | Methyl Ethyl Ketone Loaded Micrograms | Methyl Ethyl Ketone Recovered Micrograms | Recovered % |
|---|---|---|---|
| 1 | 2406 | 2121 | 88.2 |
| 2 | 2406 | 2114 | 87.9 |
| 3 | 2406 | 2162 | 90.0 |

Control C Recovery of Methyl Phenyl Ketone from Coconut Shell Charcoal

The procedure described in Control A was used with the exception that 2052 micrograms of methyl phenyl ketone (acetophenone) was injected onto the coconut shell charcoal sample tube. The recovery data obtained are delineated in Table 5.

TABLE 5
(Control C)
RECOVERY OF METHYL PHENYL KETONE
FROM COCONUT SHELL CHARCOAL

| Sample No. | Methyl Phenyl Ketone Loaded Micrograms | Methyl Phenyl Ketone Recovered Micrograms | Recovered % |
|---|---|---|---|
| 1 | 2052 | 1364 | 66.5 |
| 2 | 2052 | 1282 | 62.5 |
| 3 | 2052 | 1312 | 63.9 |

EXAMPLE 6

Recovery of Methyl Phenyl Ketone from Beaded Activated Carbon

The procedure described in Control A was used with the exception that 2052 micrograms of methyl phenyl ketone was injected onto the beaded activated carbon sample tube. The recovery data are shown in Table 6.

TABLE 6
(Example 6)
RECOVERY OF METHYL PHENYL KETONE
FROM BEADED ACTIVATED CARBON

| Sample No. | Methyl Phenyl Ketone Loaded Micrograms | Methyl Phenyl Ketone Recovered Micrograms | Recovered % |
|---|---|---|---|
| 1 | 2052 | 1622 | 79.0 |
| 2 | 2052 | 1638 | 79.8 |
| 3 | 2052 | 1648 | 80.3 |

Control D Recovery of Methyl Isobutyl Ketone from Coconut Shell Charcoal

The procedure described in Control A was used with the exception that 1596 micrograms of methyl isobutyl ketone was injected onto the coconut shell charcoal sample tube. The resulting recovery data is presented in Table 7.

TABLE 7
(Control D)
RECOVERY OF METHYL ISOBUTYL KETONE
FROM COCONUT SHELL CHARCOAL

| Sample No. | Methyl Isobutyl Ketone Loaded Micrograms | Methyl Isobutyl Ketone Recovered Micrograms | Recovered % |
|---|---|---|---|
| 1 | 1596 | 1298 | 81.3 |
| 2 | 1596 | 1294 | 81.1 |
| 3 | 1596 | 1292 | 81.0 |

EXAMPLE 7

Recovery of Methyl Isobutyl Ketone from Beaded Activated Carbon

The procedure described in Control A was used with the exception that 1596 micrograms of methyl isobutyl ketone was injected onto the beaded activated carbon sample tube. The data are delineated in Table 8.

TABLE 8
(Example 7)
RECOVERY OF METHYL ISOBUTYL KETONE
FROM BEADED ACTIVATED CARBON

| Sample No. | Methyl Isobutyl Ketone Loaded Micrograms | Methyl Isobutyl Ketone Recovered Micrograms | Recovered % |
|---|---|---|---|
| 1 | 1596 | 1488 | 93.2 |
| 2 | 1596 | 1482 | 92.9 |
| 3 | 1596 | 1508 | 94.5 |

Control E Recovery of Mesityl oxide from Coconut Shell Charcoal

The procedure described in Control A was used with the exception that 856 micrograms of mesityl oxide was injected onto the coconut shell charcoal sample tube. The desorption data are delineated in Table 9.

TABLE 9

(Control E)
RECOVERY OF MESITYL OXIDE
FROM COCONUT SHELL CHARCOAL

| Sample No. | Mesityl Oxide Loaded Micrograms | Mesityl Oxide Recovered Micrograms | Recovered % |
|---|---|---|---|
| 1 | 856 | 668 | 78.0 |
| 2 | 856 | 723 | 84.5 |
| 3 | 856 | 720 | 84.1 |

EXAMPLE 8

Recovery of Mesityl Oxide from Beaded Activated Carbon

The procedure described in Control A was used to load and recover 856 micrograms of mesityl oxide from beaded activated carbon sample tubes. The results are shown in Table 10.

TABLE 10

(Example 8)
RECOVERY OF MESITYL OXIDE
FROM BEADED ACTIVATED CARBON

| Sample No. | Mesityl Oxide Loaded Micrograms | Mesityl Oxide Recovered Micrograms | Recovered % |
|---|---|---|---|
| 1 | 856 | 749 | 87.5 |
| 2 | 856 | 802 | 93.7 |
| 3 | 856 | 759 | 88.7 |

EXAMPLE 9

Recovery of Diisobutyl Ketone From Beaded Activated Carbon

Recovery data from diisobutyl ketone from beaded activated carbon is presented in Table 11. Control samples, (diisobutyl ketone from coconut shell charcoal) were not done.

TABLE 11

(Example 9)
RECOVERY OF DIISOBUTYL KETONE
FROM BEADED ACTIVATED CARBON

| Sample No. | Diisobutyl Ketone Loaded Micrograms | Diisobutyl Ketone Recovered Micrograms | Recovered % |
|---|---|---|---|
| 1 | 723 | 703 | 97.2 |
| 2 | 723 | 711 | 98.3 |
| 3 | 723 | 708 | 97.9 |
| 4 | 1445 | 1436 | 99.4 |
| 5 | 1445 | 1454 | 100.6 |
| 6 | 1445 | 1292 | 89.4 |

EXAMPLE 10

Recovery of Diethyl Ketone, Dipropyl Ketone, and Methyl Isoamyl Ketone From Beaded Activated Carbon The following recovery data in Table 12 has been recorded for the three ketones, diethyl ketone, dipropyl ketone and methyl isoamyl ketone. These data do not include pulling humidified air through the tube as was done for all other data in this application:

TABLE 12

(Example 10)
RECOVERY OF DIETHYL, DIPROPYL, AND
METHYL ISOAMYL KETONE FROM BEADED
ACTIVATED CARBON

| Compound | Number of Samples | Loading Micrograms | Average Recovery |
|---|---|---|---|
| Diethyl Ketone | 6 | 3498 | 95.0% |
| Dipropyl Ketone | 6 | 1140 | 95.8% |
| Methyl Isoamyl Ketone | 6 | 1134 | 91.5% |

For the quantitative analysis of ketones in air using the procedures of this invention, the actual weight of ketone recovered from the sample tube are corrected by multiplying the recovered weight by a factor based on the predetermined percent recovery for that compound e.g., 80% yields a factor of 1.25.

Another point of superiority of beaded activated carbon over coconut shell charcoal lies in the physical results obtained when carbon disulfide is added to the adsorbent in the desorption vial particularly if the adsorbent has been exposed to humidified air during sample collection. Coconut shell charcoal agglomerated in clumps which adhere to the walls of the vial thus preventing good contact with the carbon disulfide during shaking or agitation. In contrast, beaded activated carbon did not agglomerate but remained as separate beads which settled to the bottom of the vials thus providing superior solvent carbon contact during shaking.

Although the invention has been described in its preferred forms with a certain degree of particularity, it is understood that the present disclosure has been made only by way of example and that numerous changes can be made without departing from the spirit and the scope of this invention.

We claim:

1. Method of assaying ketones in ambient air, said ketones being selected from the group consisting of cyclohexanone, methyl ethyl ketone, methyl phenyl ketone, methyl isobutyl ketone and mesityl oxide, said method consisting essentially of:
   (a) contacting a known volume of ambient air containing at least one of said ketones, at an ambient temperature with an excess of beaded activated carbon whereby one or more of said ketones is adsorbed onto the beaded activated carbon;
   (b) contacting the beaded activated carbon containing one or more adsorbed ketones from step (a) with a solvent for ketones whereby said one or more adsorbed ketones are desorbed from the beaded activated carbon forming a solution of one or more of said ketones in said solvent;
   (c) recovering the solution of one or more ketones from step (b); and
   (d) analyzing the solution of one or more ketones for ketone content.

2. Method claimed in claim 1 wherein the cycloaliphatic ketone is cyclohexanone.

3. Method claimed in claim 1 wherein the ketone is methyl ethyl ketone.

4. Method claimed in claim 1 wherein the ketone is methyl phenyl ketone.

5. Method claimed in claim 1 wherein the ketone is mesityl oxide.

6. Method claimed in claim 1 wherein the ketone solvent in step (B) is carbon disulfide.

7. Method as in claim 1 wherein the ketone is methyl isobutyl ketone.

* * * * *